(12) United States Patent
Suzuki et al.

(10) Patent No.: US 12,727,819 B2
(45) Date of Patent: Sep. 8, 2026

(54) PHYSIOLOGICAL INFORMATION PROCESSING SYSTEM, SIGNAL PROCESSING DEVICE, SWITCHING DEVICE, AND NON-TRANSITORY COMPUTER-READABLE STORAGE MEDIUM

(71) Applicant: NIHON KOHDEN CORPORATION, Tokyo (JP)

(72) Inventors: Tetsuo Suzuki, Tokorozawa (JP); Yoshiharu Harada, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 681 days.

(21) Appl. No.: 18/175,068

(22) Filed: Feb. 27, 2023

(65) Prior Publication Data

US 2023/0277128 A1 Sep. 7, 2023

(30) Foreign Application Priority Data

Mar. 4, 2022 (JP) ................................ 2022-033313

(51) Int. Cl.
*A61B 5/00* (2006.01)

(52) U.S. Cl.
CPC ............. *A61B 5/6801* (2013.01); *A61B 5/72* (2013.01)

(58) Field of Classification Search
CPC ................................ A61B 5/6801; A61B 5/72
See application file for complete search history.

(56) References Cited

U.S. PATENT DOCUMENTS

2017/0196463 A1 7/2017 Suzuki et al.
2021/0251536 A1* 8/2021 Al-Ali ................ A61B 5/14551

FOREIGN PATENT DOCUMENTS

JP 2017-123093 A 7/2017

* cited by examiner

*Primary Examiner* — Lindsey G Wehrheim
(74) *Attorney, Agent, or Firm* — Sughrue Mion, PLLC

(57) ABSTRACT

A signal processing device is mounted on a physiological information processing device switchable between a first state in which the physiological information processing device is operable by a first function and a second state in which the physiological information processing device is operable by a second function higher than the first function. The signal processing device processes a signal corresponding to physiological information output from a sensor included in a probe connected to the physiological information processing device based on a state designation information for designating whether the physiological information processing device operates in the first state or in the second state. The signal processing device, when the probe holding type specific information is connected to the physiological information processing device, receive the type specific information, and when a switching device holding switching information is connected to the physiological information processing device, receive the switching information.

4 Claims, 5 Drawing Sheets

FIG. 4

| CASE NUMBER | TYPE SPECIFIC INFORMATION | SWITCHING REQUEST | PERMIT REWRITING | STATE DESIGNATION INFORMATION | OPERATION |
|---|---|---|---|---|---|
| 1 | FIRST STATE | NOT REQUESTED | NOT PERMITTED | FIRST STATE | FIRST STATE |
| 2 | SECOND STATE | NOT REQUESTED | NOT PERMITTED | FIRST STATE | FIRST STATE |
| 3 | FIRST STATE | REQUESTED | NOT PERMITTED | FIRST STATE | FIRST STATE |
| 4 | SECOND STATE | REQUESTED | NOT PERMITTED | FIRST STATE | FIRST STATE |
| 5 | FIRST STATE | NOT REQUESTED | PERMITTED | FIRST STATE | FIRST STATE |
| 6 | SECOND STATE | NOT REQUESTED | PERMITTED | FIRST STATE | FIRST STATE |
| 7 | FIRST STATE | REQUESTED | PERMITTED | FIRST STATE | FIRST STATE |
| 8 | SECOND STATE | REQUESTED | PERMITTED | SECOND STATE | SECOND STATE |
| 9 | FIRST STATE | REQUESTED | PERMITTED | SECOND STATE | NO OPERATION |

PHYSIOLOGICAL INFORMATION PROCESSING SYSTEM, SIGNAL PROCESSING DEVICE, SWITCHING DEVICE, AND NON-TRANSITORY COMPUTER-READABLE STORAGE MEDIUM

CROSS-REFERENCE TO RELATED APPLICATIONS

The present application claims the benefit of priority of Japanese Patent Application No. 2022-033313, filed on Mar. 4, 2022, the content of which is incorporated herein by reference.

TECHNICAL FIELD

The disclosure relates to a system for processing physiological information of a subject. The disclosure also relates to a signal processing device and a switching device each of which can constitute a part of the system. The disclosure also relates to a non-transitory computer-readable storage medium storing a program executable by a processor mounted on the signal processing device.

BACKGROUND

JP2017-123093A discloses a physiological information processing system including a probe and a physiological information processing device. The probe can include a sensor and an information element. The sensor is attached to a living body and is configured to output a signal corresponding to physiological information. The information element includes information for specifying a sensor. When the probe is connected to the physiological information processing device, information on the information element is read by the physiological information processing device. The physiological information processing device performs an operation according to the information.

SUMMARY

The present disclosure is provided with a physiological information processing system that can be flexibly operated in accordance with the specifications of a probe.

An aspect of the present disclosure of a physiological information processing system including:

- a physiological information processing device connected to a probe and switchable between a first state in which the physiological information processing device is operable by a first function and a second state in which the physiological information processing device is operable by a second function higher than the first function, the probe including a sensor configured to output a signal corresponding to physiological information and a first information element holding type specific information for specifying a type of the sensor;
- a storage mounted on the physiological information processing device and configured to store state designation information for designating whether the physiological information processing device operates in the first state or in the second state;
- a first switching device connectable to the physiological information processing device and including a second information element that holds first switching information for requesting switching from the first state to the second state;

- a control device mounted on the physiological information processing device and configured to define whether the state designation information is permitted; and
- a signal processing device mounted on the physiological information processing device, and configured to receive the type specific information and process the signal based on the state designation information when the probe is connected to the physiological information processing device, and receive the first switching information when the first switching device is connected to the physiological information processing device,
- wherein the signal processing device rewrites the state designation information so as to designate an operation in the second state when the control device permits rewriting of the state designation information, the signal processing device receives a request for switching from the first state to the second state by the first switching information, and the probe including the first information element in which the type specific information for specifying a type of the sensor suitable for an operation in the second function is held is connected to the physiological information processing device.

An aspect of the present disclosure of a signal processing device that is mounted on a physiological information processing device switchable between a first state in which the physiological information processing device is operable by a first function and a second state in which the physiological information processing device is operable by a second function higher than the first function, and processes a signal corresponding to physiological information output from a sensor included in a probe connected to the physiological information processing device, the signal processing device including:

- a processor configured to process the signal based on state designation information for designating whether the physiological information processing device operates in the first state or in the second state; and
- an interface configured to, when the probe holding type specific information for specifying a type of the sensor is connected to the physiological information processing device, receive the type specific information, and when a switching device holding switching information for requesting switching from the first state to the second state is connected to the physiological information processing device, receive the switching information,
- wherein the processor rewrites the state designation information so as to designate an operation in the second state when rewriting of the state designation information is permitted, a request for switching from the first state to the second state based on the switching information is received, and the type specific information specifies a type of the sensor suitable for an operation in the second function.

An aspect of the present disclosure of a non-transitory computer-readable storage medium storing a computer program for causing a processor of a signal processing device that is mounted on a physiological information processing device switchable between a first state in which the physiological information processing device is operable by a first function and a second state in which the physiological information processing device is operable by a second function higher than the first function, and processes a signal corresponding to physiological information output from a sensor included in a probe connected to the physiological information processing device, the computer program that causes the signal processing device to execute:

processing the signal based on state designation information for designating whether the physiological information processing device operates in the first state or in the second state;

when the probe holding type specific information for specifying a type of the sensor is connected to the physiological information processing device, receiving the type specific information;

when a switching device holding switching information for requesting switching from the first state to the second state is connected to the physiological information processing device, receiving the switching information; and when rewriting of the state designation information is permitted, a request for switching from the first state to the second state by the switching information is received, and the type specific information specifies a type of sensor suitable for an operation in the second function, rewriting the state designation information so as to designate an operation in the second state.

According to the configuration as described above, switching from the first state to the second state is not immediately performed by connecting the first switching device to the physiological information processing device, but switching to the second state can be suspended until the probe suitable for the operation in the second function is connected to the information processing device and rewriting of the state designation information is permitted by the control device. Since a timing at which the first switching device is connected to the information processing device and a timing at which the operation in the second function is actually enabled by rewriting the state designation information so as to designate the second state can be made different depending on various circumstances, the use of the probe suitable for the operation in the first function can be continued even after the first switching device is connected to the information processing device. Therefore, it is possible to provide a physiological information processing system that can be flexibly operated in accordance with the specifications of the probe.

An aspect of the present disclosure of a switching device including:

a connector connectable to a physiological information processing device that is switchable between a first state in which the physiological information processing device is operable by a first function and a second state in which the physiological information processing device is operable by a second function higher than the first function; and an information element holding switching information for switching the physiological information processing device from the second state to the first state by being received by a signal processing device mounted on the physiological information processing device through the connector.

In general, a probe suitable for the operation in the first function cannot be used even if the probe is connected to the information processing device for which an operation in the second state is designated. According to the above configuration, the information processing device switched to the second state can be returned to the first state as necessary. As a result, the use of the probe suitable for the operation in the first function in the information processing device can be resumed. Therefore, a physiological information processing system that can be flexibly operated in accordance with the specifications of the probe is provided.

BRIEF DESCRIPTION OF DRAWINGS

FIG. 4 illustrates a plurality of states that the physiological information processing device can take.

DESCRIPTION OF EMBODIMENTS

Figure 1:
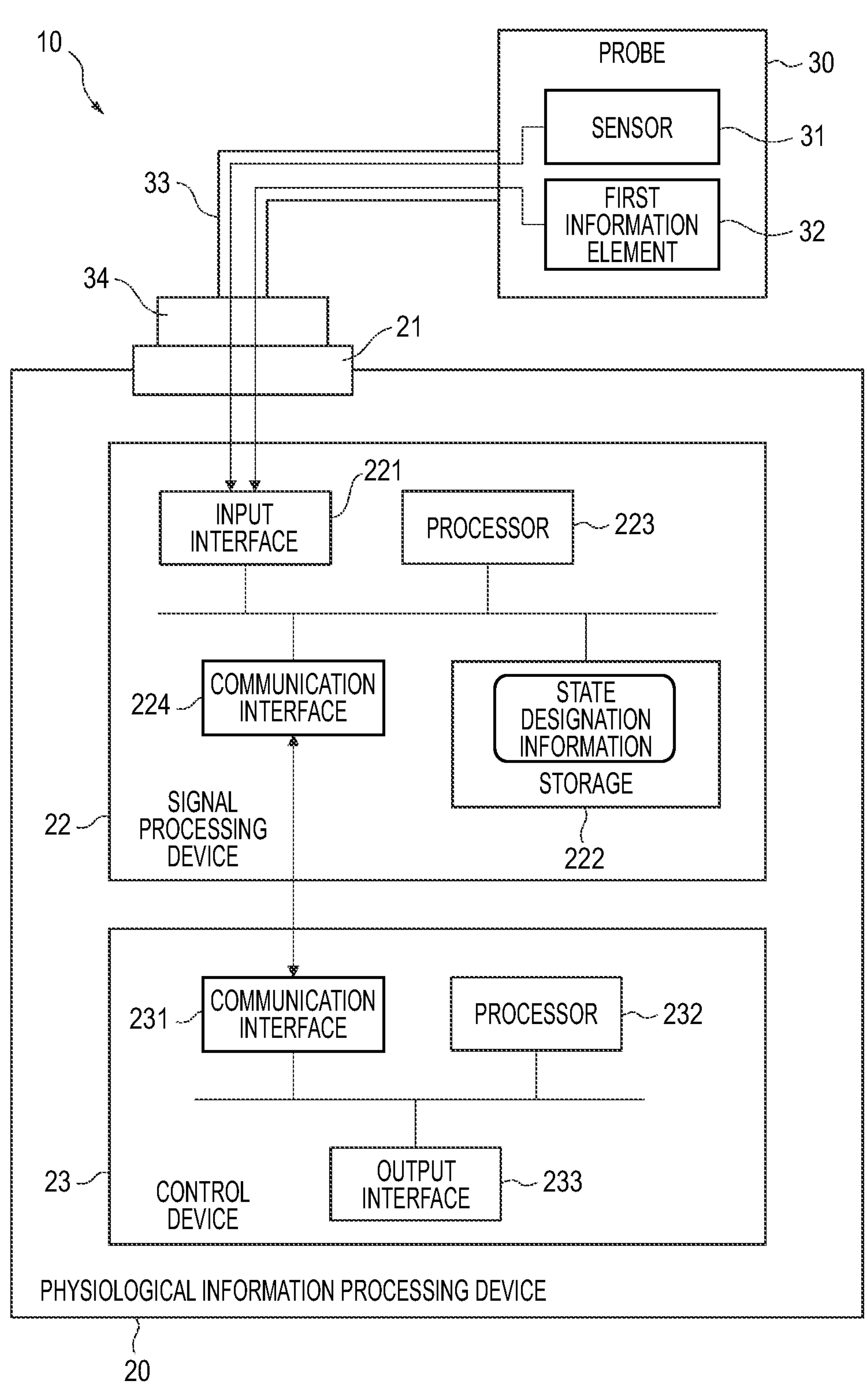
FIG. 1 illustrates a state in which a probe is connected to a physiological information processing device in a physiological information processing system according to an embodiment.

Hereinafter, examples of an embodiment will be described in detail with reference to the accompanying drawings. In the drawings, the scale is changed as appropriate in order to make the illustrated elements recognizable.

FIG. 1 illustrates a functional configuration of a physiological information processing system 10 (hereinafter abbreviated as an information processing system 10) according to the embodiment.

The information processing system 10 can include a physiological information processing device 20 (hereinafter, abbreviated as an information processing device 20). The information processing device 20 can include a connector 21 to which a probe 30 is connected. The probe 30 is a device that is attached to a subject and acquires physiological information on the subject.

The information processing device 20 is switchable between a first state in which the information processing device 20 is operable by a first function and a second state in which the information processing device 20 is operable by a second function higher than the first function. In the present specification, an expression "a second function higher than the first function" is used for depicting a case where the number of the types of physiological information that can be acquired by the second function is larger than the number of the types of physiological information that can be acquired by the first function, a case where an information amount of specific physiological information that can be acquired by the second function is larger than an information amount of the physiological information that can be acquired by the first function, a case where a resolution of the specific physiological information that can be acquired by the second function is higher than a resolution of the physiological information that can be acquired by the first function, and the like.

The probe 30 can include a sensor 31. The sensor 31 is configured to output a detection signal corresponding to the physiological information on the subject. The detection signal may be an analog signal or a digital signal. An example of the sensor 31 is an optical sensor having a light emitting element and a light receiving element. In this case, a blood light absorber concentration and the pulse are detected as the physiological information. Another example of the sensor 31 is a catheter that is inserted into a blood vessel and has a pressure transducer. In this case, the blood pressure is detected as the physiological information.

The probe 30 can include a first information element 32. The first information element 32 holds type specific information for specifying the type of the sensor 31. The expression "the type of the sensor 31" used here means that the sensor 31 is a model suitable for either the first function or the second function. Examples of the first information element 32 include a memory in which type specific information is stored, and a value of a specific circuit element associated with the type specific information (a value of a resistance element, a value of a capacitor element, a value of an inductor element, and a forward drop voltage of a diode).

In the information processing system 10 according to the present embodiment, it is assumed that the probe 30 suitable for the operation in the first function cannot be used even if the probe 30 is connected to the information processing device 20 for which an operation in the second state is designated.

The probe 30 can include a cable 33 and a connector 34. The cable 33 can include a signal line that transmits the detection signal output from the sensor 31. The connector 34 is provided at one end of the cable 33. The connector 34 is connected to the connector 21 of the information processing device 20. The first information element 32 may be disposed at any position in the probe 30 including the cable 33 and the connector 34.

The information processing device 20 can include a signal processing device 22. The signal processing device 22 is a device that performs signal processing so that physiological information acquired through the probe 30 can be provided in a form recognizable by a user. The signal processing device 22 can include an input interface 221, a storage 222, a processor 223, and a communication interface 224.

The information processing device 20 can include a control device 23. The control device 23 is a device that controls an operation of the information processing device 20. The operation includes providing the physiological information acquired through the probe 30 in a form recognizable by the user. The control device 23 can include a communication interface 231, a processor 232, and an output interface 233.

The input interface 221 is configured to receive a detection signal input to the connector 21. When the detection signal is an analog signal, the input interface 221 can include an appropriate conversion circuit including an A/D converter. This description is applied to all signals and information that can be received by the input interface 221 described below.

The input interface 221 is configured to acquire the type specific information held in the first information element 32 of the probe 30 through the connector 21.

The storage 222 stores state designation information. The state designation information is used for designating whether the information processing device 20 operates in the first state or the second state. The storage 222 may be implemented by a nonvolatile semiconductor memory or a hard disk device.

The processor 223 is configured to refer to the state designation information stored in the storage 222. The processor 223 is configured to operate the information processing device 20 in the first state or the second state based on the referred state designation information. Specifically, when the state designation information designates the first state, the processor 223 performs signal processing related to the first function on the detection signal received by the input interface 221. When the state designation information designates the second state, the processor 223 performs signal processing related to the second function on the detection signal received by the input interface 221.

The communication interface 224 of the signal processing device 22 and the communication interface 231 of the control device 23 are capable of bidirectional communication of signals and data therebetween.

The processor 223 of the signal processing device 22 is configured to output the processed information acquired as a result of the signal processing from the communication interface 224. The information is received by the communication interface 231 of the control device 23. The processor 232 of the control device 23 is configured to output an output signal to be provided to the user through a user interface from the output interface 233 based on the information. As an example, the output signal may be a signal for displaying processed information on a display device (not illustrated) mounted on the information processing device 20. As another example, the output signal may be a signal for transmitting processed information to an external device (not illustrated) communicably connected to the information processing device 20.

The output signal may be an analog signal or a digital signal. When the output signal is an analog signal, the output interface 233 can include an appropriate conversion circuit including a D/A converter.

The control device 23 also has a function of defining whether to rewrite the state designation information stored in the storage 222 of the signal processing device 22. Specifically, the processor 232 of the control device 23 is configured to be able to transmit a permission signal for permitting rewriting of the state designation information from the communication interface 231 to the signal processing device 22.

The transmission of the permission signal may be automatically performed at the time of activation of the information processing device 20, or may be performed in response to a user instruction input through a user interface of the information processing device 20.

Figure 2:
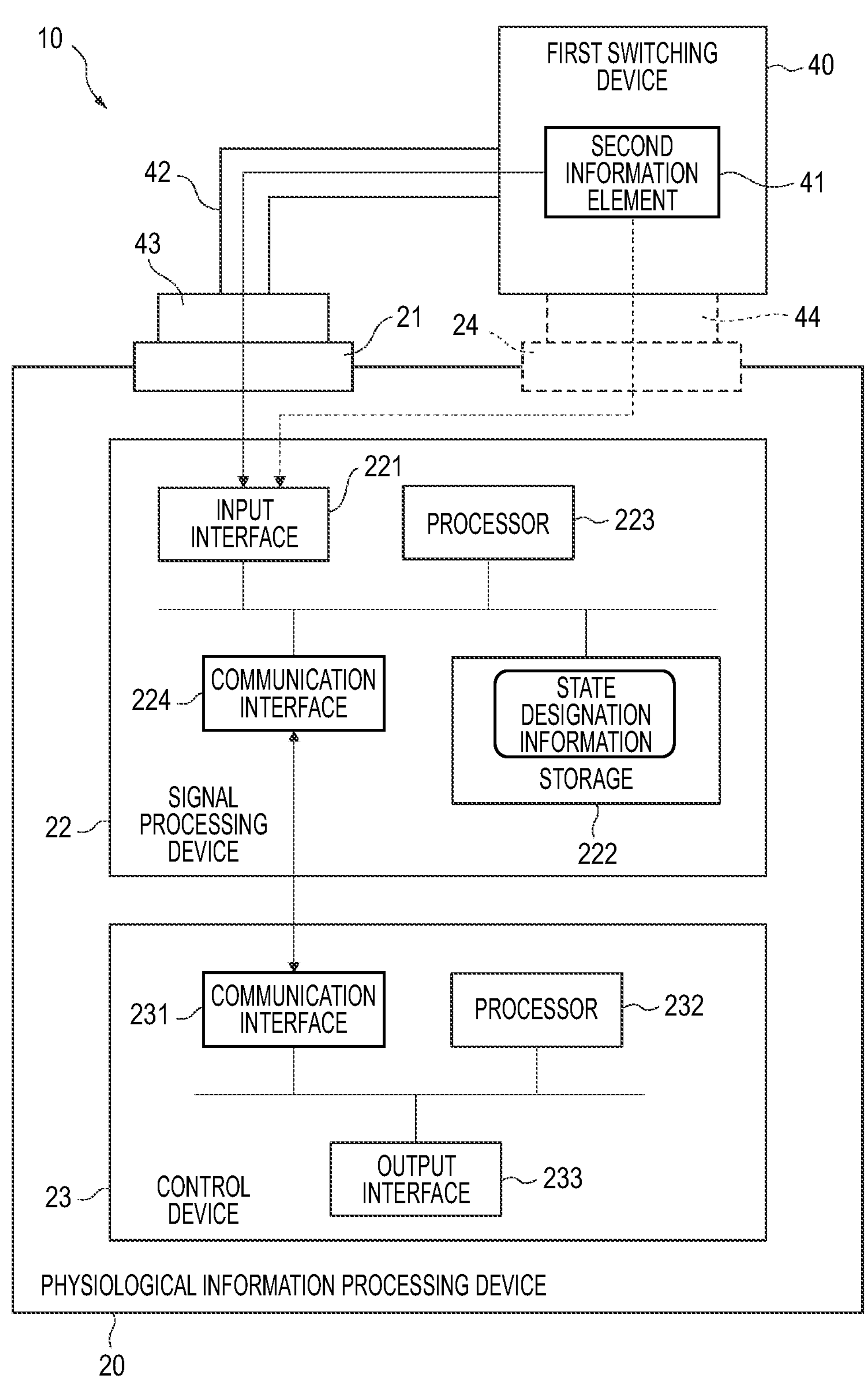
FIG. 2 illustrates a state in which a first switching device is connected to the physiological information processing device in the physiological information processing system according to the embodiment.

As illustrated in FIG. 2, the information processing system 10 can include a first switching device 40. The first switching device 40 is a device connected to the information processing device 20 in order to switch the information processing device 20 from the first state to the second state.

The first switching device 40 can include a second information element 41. The second information element 41 holds first switching information for requesting switching from the first state to the second state. Examples of the second information element 41 include a memory in which the first switching information is stored, and a value of a specific circuit element associated with the first switching information (a value of a resistance element, a value of a capacitor element, a value of an inductor element, and a forward drop voltage of a diode).

When the first switching device 40 is connected to the information processing device 20, the processor 223 of the signal processing device 22 is configured to acquire the first switching information through the input interface 221. The first switching information once acquired is held even when power supply to the information processing device 20 is cut off.

In order to switch the information processing device 20 from the first state to the second state, it is necessary to satisfy that (1) rewriting of the state designation information is permitted, (2) switching from the first state to the second state is requested, and (3) the probe including the first information element 32 in which the type specific information for specifying the type of a sensor suitable for the operation in the second function is held is connected to the information processing device 20.

When the probe 30 including the first information element 32 in which the type specific information suitable for the operation in the second function is held is connected to the connector 21 after the first switching information is held by the first switching device 40 being connected to the information processing device 20, the processor 223 of the signal processing device 22 is configured to determine whether the permission signal is received from the control device 23. When it is determined that the permission signal is received, the processor 223 is configured to rewrite the state designation information stored in the storage 222 so as to designate the operation in the second state. Thereafter, since the rewritten state designation information is referred to by the processor 223, the signal processing related to the second function is performed on the detection signal output from the sensor 31.

Figure 3:
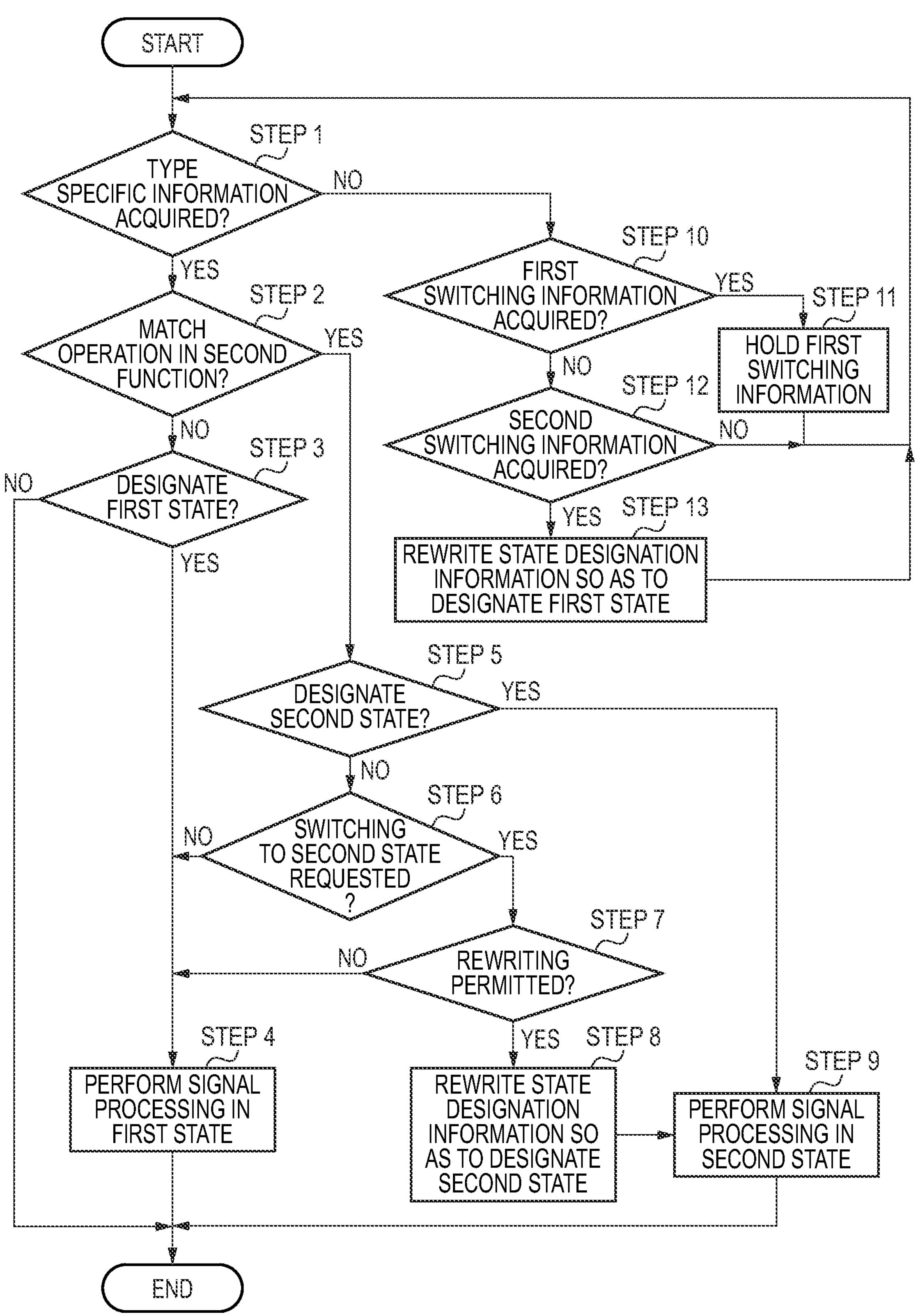
FIG. 3 illustrates a flow of processing performed by a signal processing device mounted on the physiological information processing device.

The operation of the information processing system 10 configured as described above will be described with reference to FIGS. 3 and 4. FIG. 3 illustrates a flow chart of processing performed by the processor 223 of the signal processing device 22. FIG. 4 illustrates a relationship between a state of each element constituting a switching condition and the operation of the information processing device 20.

The processor 223 determines whether the type specific information is acquired through the input interface 221 (STEP 1). When the type specific information is acquired (YES in STEP 1), the probe 30 is connected to the information processing device 20.

Subsequently, the processor 223 determines whether the type of the sensor specified by the acquired type specific information matches the operation in the second function (STEP 2). When the type of the sensor specified by the acquired type specific information matches the operation in the first function (NO in STEP 2), the processor 223 determines whether the state designation information stored in the storage 222 designates the first state (STEP 3).

When it is determined that the state designation information designates the first state (YES in STEP 3), the processor 223 performs the signal processing related to the first function on the detection signal output from the sensor 31 (STEP 4). In other words, the information processing device 20 operates in the first state.

This situation corresponds to case numbers 1, 3, 5, and 7 in FIG. 4. That is, regardless of whether the rewriting of the state designation information is permitted, when the probe 30 suitable for the operation in the first function is connected in a state where the state designation information designates the first state, the information processing device 20 operates in the first state.

On the other hand, when the type of the sensor specified by the acquired type specific information matches the operation in the second function (YES in STEP 2), the processor 223 determines whether the state designation information stored in the storage 222 designates the second state (STEP 5).

When it is determined that the state designation information designates the first state (NO in STEP 5), the processor 223 determines whether switching from the first state to the second state is requested (STEP 6). That is, the processor 223 determines whether the first switching device 40 is connected to the information processing device 20 before the connection between the information processing device 20 and the probe 30 suitable for the operation in the second function.

When it is determined that the switching from the first state to the second state is not requested (NO in STEP 6), the processor 223 performs signal processing related to the first function on the detection signal output from the sensor 31 (STEP 4). In other words, the information processing device 20 operates in the first state even when the probe 30 suitable for the operation in the second function is connected thereto. This situation corresponds to case numbers 2 and 6 in FIG. 4.

When it is determined that switching from the first state to the second state is requested (YES in STEP 6), the processor 223 determines whether rewriting of the state designation information is permitted by the control device 23 (STEP 7).

When the rewriting of the state designation information is not permitted (NO in STEP 7), the processor 223 performs signal processing related to the first function on the detection signal output from the sensor 31 (STEP 4). In other words, the information processing device 20 operates in the first state even when the probe 30 suitable for the operation in the second function is connected thereto. This situation corresponds to a case number 4 in FIG. 4.

When the rewriting of the state designation information is permitted (YES in STEP 7), the processor 223 rewrites the state designation information stored in the storage 222 so as to designate the second state (STEP 8).

Subsequently, the processor 242 performs signal processing related to the second function on the detection signal output from the sensor 31 (STEP 9). In other words, the information processing device 20 operates in the second state. This situation corresponds to a case number 8 in FIG. 4.

Even when the probe 30 suitable for the operation in the second function is connected to the information processing device 20 in a situation where the state designation information designates the second state (YES in STEP 1, YES in STEP 2, and YES in STEP 5), the information processing device 20 operates in the second state (STEP 9). This situation also corresponds to the case number 8 in FIG. 4.

When it is determined that the type specific information is not acquired through the input interface 241 (NO in STEP 1), the processor 223 determines whether the first switching information is acquired through the input interface 221 (STEP 10). That is, the processor 223 determines whether the first switching device 40 is connected to the information processing device 20.

When it is determined that the first switching information is acquired (YES in STEP 10), the processor 223 holds the first switching information (STEP 11). The first switching information may be stored in the storage 222 or may be stored in another storage area. Thereafter, the process returns to STEP 1.

According to the configuration as described above, the switching from the first state to the second state is not immediately performed by connecting the first switching device 40 to the information processing device 20, but switching to the second state can be suspended until the probe 30 suitable for the operation in the second function is connected to the information processing device 20 and rewriting of the state designation information is permitted by the control device 23. Since a timing at which the first switching device 40 is connected to the information processing device 20 and a timing at which the operation in the second function is actually enabled by rewriting the state designation information so as to designate the second state can be made different depending on various circumstances, the use of the probe 30 suitable for the operation in the first function can be continued even after the first switching device 40 is connected to the information processing device 20. Therefore, it is possible to provide the physiological information processing system 10 that can be flexibly operated in accordance with the specification of the probe 30.

As described above, the probe 30 suitable for the operation in the first function cannot be used even if the probe 30 is connected to the information processing device 20 for which the operation in the second state is designated. That is, when it is detected that the probe 30 suitable for the operation in the first function is connected to the information processing device 20 and the state designation information designates the second state (YES in STEP 1, NO in STEP 2, and NO in STEP 3), the processor 223 ends the process without operating the information processing device 20 in the first state. This situation corresponds to a case number 9 in FIG. 4.

Figure 5:
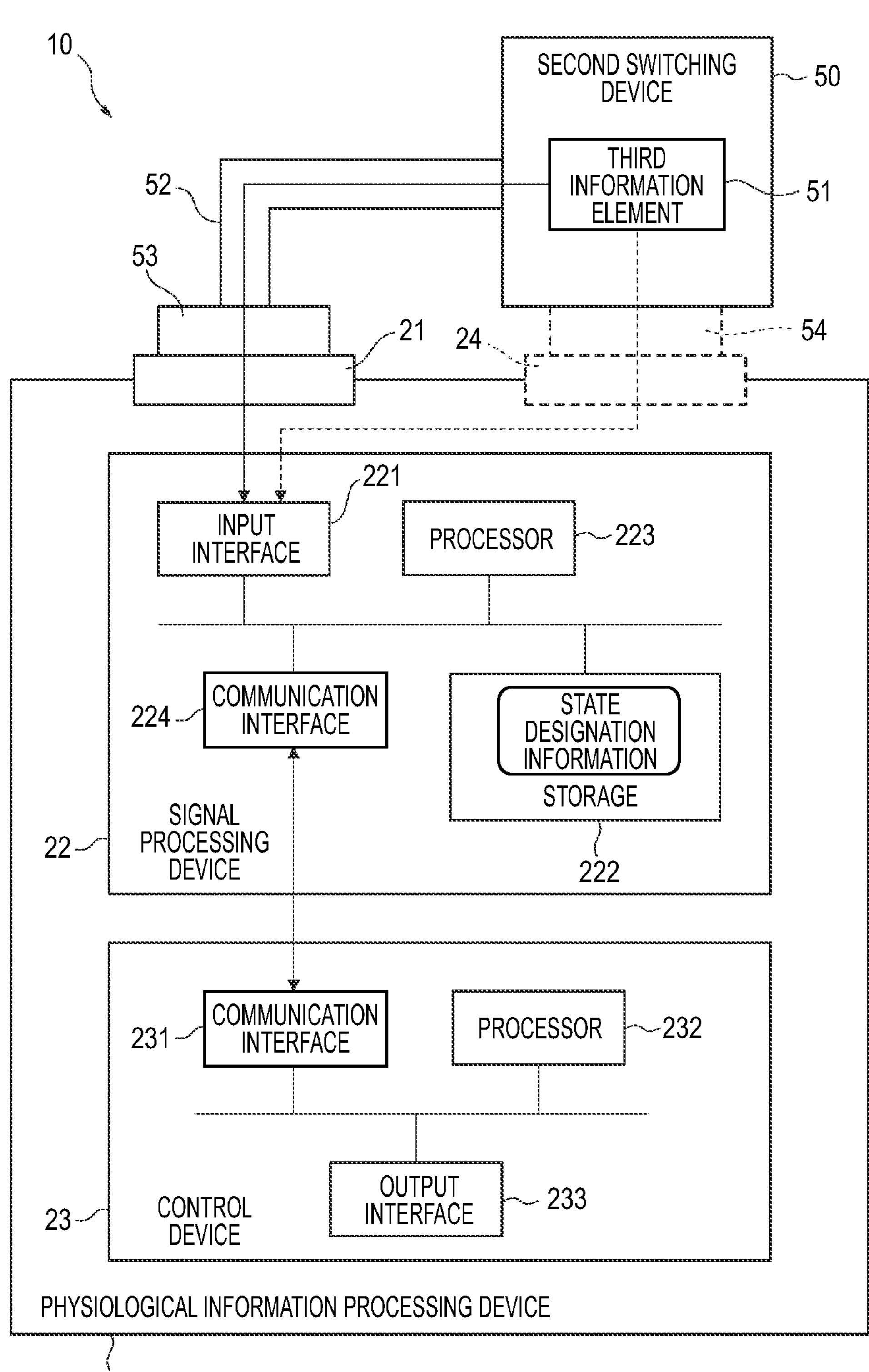
FIG. 5 illustrates a state in which a second switching device is connected to the physiological information processing device in the physiological information processing system according to the embodiment.

As illustrated in FIG. 5, the information processing system 10 may include a second switching device 50. The second switching device 50 is a device connected to the information processing device 20 in order to switch the information processing device 20 from the second state to the first state.

The second switching device 50 can include a third information element 51. The third information element 51 holds second switching information for requesting switching from the second state to the first state. Examples of the third information element 51 include a memory in which the second switching information is stored, and a value of a specific circuit element associated with the second switching information (a value of a resistance element, a value of a capacitor element, a value of an inductor element, and a forward drop voltage of a diode).

When the second switching device 50 is connected to the information processing device 20, the processor 223 of the signal processing device 22 is configured to acquire the second switching information through the input interface 221.

In this example, when it is determined that neither the type specific information nor the first switching information is acquired through the input interface 221 (NO in STEP 1 and NO in STEP 10 in FIG. 3), the processor 223 determines whether the second switching information is acquired through the input interface 221 (STEP 12). That is, the processor 223 determines whether the second switching device 50 is connected to the information processing device 20.

When it is determined that the second switching information is acquired (YES in STEP 12), the processor 223 rewrites the state designation information stored in the storage 222 so as to designate the first state (STEP 13). Thereafter, the process returns to STEP 1.

When it is determined that the second switching information is not acquired (NO in STEP 12), the processor 242 determines that no device is connected to the information processing device 20, and returns the process to STEP 1.

In general, a probe suitable for the operation in the first function cannot be used even if the probe is connected to the information processing device for which an operation in the second state is designated. According to such a configuration, the information processing device 20 switched to the second state can be returned to the first state as necessary. Therefore, the use of the probe 30 suitable for the operation in the first function in the information processing device 20 can be resumed. As a result, it is possible to further increase the flexibility related to the operation of the information processing system 10.

As illustrated in FIG. 2, the first switching device 40 can include a cable 42 and a connector 43. The cable 42 can include a signal line used for acquiring the first switching information by the signal processing device 22. The connector 43 is provided at one end of the cable 42. The connector 43 is connected to the connector 21 of the information processing device 20. That is, the first switching device 40 is connected to the connector 21 to which the probe 30 is connected. The second information element 41 may be disposed at any position in the first switching device 40 including the cable 42 and the connector 43.

According to such a configuration, at least a part of the first switching device 40 excluding the second information element 41 can be formed by a component common to the probe 30. Since it is possible to reduce the cost related to the design and manufacturing of the components unique to the first switching device 40, it is possible to prevent an increase in the operation cost of the information processing system 10.

However, as illustrated in FIG. 2, the information processing device 20 can include a connector 24 different from the connector 21. In this case, the first switching device 40 may include a connector 44 connected to another connector 24. The cable 42 may be omitted.

As illustrated in FIG. 5, the second switching device 50 can include a cable 52 and a connector 53. The cable 52 can include a signal line used for acquiring the second switching information by the signal processing device 22. The connector 53 is provided at one end of the cable 52. The connector 53 is connected to the connector 21 of the information processing device 20. That is, the second switching device 50 is connected to the connector 21 to which the probe 30 is connected. The third information element 51 may be disposed at any position in the second switching device 50 including the cable 52 and the connector 53.

According to such a configuration, at least a part of the second switching device 50 excluding the third information element 51 can be formed by a component common to the probe 30. Since it is possible to reduce the cost related to the design and manufacturing of the components unique to the second switching device 50, it is possible to prevent an increase in the operation cost of the information processing system 10.

However, as illustrated in FIG. 5, the second switching device 50 can include a connector 54 connected to another connector 24. In this case, the cable 52 may be omitted. The other connector 24 may be the same as or different from the connector to which the first switching device 40 is connected.

Each of the processor 223 of the signal processing device 22 and the processor 232 of the control device 23 having the various functions described above may be implemented by a general-purpose microprocessor that operates in cooperation with a general-purpose memory. Examples of the general-purpose microprocessor include a CPU, an MPU, and a GPU. Examples of the general-purpose memory include a ROM and a RAM. In this case, ROM may store a computer program that executes the above-described processing. The ROM is an example of a non-transitory computer readable medium that stores a computer program. The general-purpose microprocessor designates at least a part of programs stored in the ROM, loads the program into a RAM, and executes the above-described processing in cooperation with the RAM. The computer program may be preinstalled in the general-purpose memory, or may be downloaded from an external server via a communication network and then installed in the general-purpose memory. In this case, the external server is an example of a non-transitory computer readable medium that stores a computer program. The storage 222 may be implemented by the general-purpose memory.

Each of the processor 223 of the signal processing device 22 and the processor 232 of the control device 23 may be implemented by a dedicated integrated circuit capable of executing the computer program, such as a microcontroller, an ASIC, or an FPGA. In this case, the computer program is preinstalled in the storage element included in the dedicated integrated circuit. The storage element is an example of a computer readable medium that stores a computer program. The storage 222 may be implemented by the storage element.

Each of the processor 223 of the signal processing device 22 and the processor 232 of the control device 23 may be implemented by a combination of a general-purpose microprocessor and a dedicated integrated circuit.

The above embodiment is merely an example for facilitating the understanding of the presently disclosed subject matter. Configurations according to the above embodiment can be appropriately changed and improved without departing from the gist of the presently disclosed subject matter.

In the above embodiment, the signal processing device 22 includes a storage for storing the state designation information. However, the storage having this function may be provided in the control device 23, or may be provided as a device independent of the signal processing device 22 and the control device 23 in the information processing device 20.

What is claimed is:

1. A physiological information processing system comprising:

a physiological information processing device connected to a probe and switchable between a first state in which the physiological information processing device is operable by a first function and a second state in which the physiological information processing device is operable by a second function higher than the first function, the probe including a sensor configured to output a signal corresponding to physiological information and a first information element holding type specific information for specifying a type of the sensor;

a storage mounted on the physiological information processing device and configured to store state designation information for designating whether the physiological information processing device operates in the first state or in the second state;

a first switching device connectable to the physiological information processing device and including a second information element that holds first switching information for requesting switching from the first state to the second state;

a second switching device connectable to the physiological information processing device, and including a third information element that holds second switching information for requesting switching from the second state to the first state;

a control device mounted on the physiological information processing device and configured to define whether the state designation information is permitted; and a signal processing device mounted on the physiological information processing device, and configured to receive the type specific information and process the signal based on the state designation information when the probe is connected to the physiological information processing device, and receive the first switching information when the first switching device is connected to the physiological information processing device, wherein the signal processing device rewrites the state designation information so as to designate an operation in the second state when the control device permits rewriting of the state designation information, the signal processing device receives a request for switching from the first state to the second state by the first switching information, and the probe including the first information element in which the type specific information for specifying a type of the sensor suitable for an operation in the second function is held is connected to the physiological information processing device, and wherein, when the second switching device is connected to the physiological information processing device, the signal processing device rewrites the state designation information so as to designate an operation in the first state based on the second switching information.

2. The physiological information processing system according to claim 1, wherein the physiological information processing device includes a connector to which the probe is connected, and, wherein at least a part of the first switching device excluding the second information element is formed by a component common to the probe, and is connectable to the connector.

3. The physiological information processing system according to claim 1, wherein the physiological information processing device includes a connector to which the probe is connected, and, wherein at least a part of the second switching device excluding the third information element is formed by a component common to the probe, and is connectable to the connector.

4. A physiological information processing system comprising:

a signal processing device that is mounted on a physiological information processing device switchable between a first state in which the physiological information processing device is operable by a first function and a second state in which the physiological information processing device is operable by a second function higher than the first function, and processes a signal corresponding to physiological information output from a sensor included in a probe connected to the physiological information processing device, a first switching device connectable to the physiological information processing device and including a first information element that holds first switching information for requesting switching from the first state to the second state; and a second switching device connectable to the physiological information processing device, and including a second information element that holds second switching information for requesting switching from the second state to the first state;

the signal processing device comprising:

a processor configured to process the signal based on state designation information for designating whether the physiological information processing device operates in the first state or in the second state; and an interface configured to, when the probe holding type specific information for specifying a type of the sensor is connected to the physiological information processing device, receive the type specific information, and when a switching device holding switching information for requesting switching from the first state to the second state is connected to the physiological information processing device, receive the switching information, wherein the processor rewrites the state designation information so as to designate an operation in the second state when rewriting of the state designation information is permitted, a request for switching from the first state to the second state based on the switching information is received, and the type specific information specifies a type of the sensor suitable for an operation in the second function, and wherein, when the second switching device is connected to the physiological information processing device, the signal processing device rewrites the state designation information so as to designate an operation in the first state based on the second switching information.

* * * * *